(12) United States Patent
Yamazaki

(10) Patent No.: US 12,313,577 B2
(45) Date of Patent: May 27, 2025

(54) SENSOR

(71) Applicant: KABUSHIKI KAISHA TOSHIBA, Tokyo (JP)

(72) Inventor: Hiroaki Yamazaki, Yokohama Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 315 days.

(21) Appl. No.: 17/823,918

(22) Filed: Aug. 31, 2022

(65) Prior Publication Data
US 2023/0288356 A1    Sep. 14, 2023

(30) Foreign Application Priority Data

Mar. 9, 2022   (JP) ................................ 2022-035782

(51) Int. Cl.
*G01N 25/18*        (2006.01)

(52) U.S. Cl.
CPC .................................... *G01N 25/18* (2013.01)

(58) Field of Classification Search
CPC ..................... G01N 25/18; G01N 25/48–4893
See application file for complete search history.

(56) References Cited

U.S. PATENT DOCUMENTS

| | | | | |
|---|---|---|---|---|
| 5,295,746 | A * | 3/1994 | Friauf .................. | G01N 25/482 |
| | | | | 374/170 |
| 8,762,075 | B2 * | 6/2014 | Loui .................... | G01N 29/036 |
| | | | | 702/24 |
| 11,867,648 | B2 * | 1/2024 | Ali ........................ | G01N 25/18 |
| 2020/0080954 | A1 | 3/2020 | Yamazaki | |

FOREIGN PATENT DOCUMENTS

JP        2020-41893 A      3/2020

OTHER PUBLICATIONS

Yumi Hayashi et al., "Integrated Hybrid MEMS Hydrogen Sensor with High Sensitivity and High Dynamic Range," IEEJ Trans. on Sensors and Micromachines, vol. 140, No. 7, pp. 158-164 (2020).
Susumu International U.S.A., "Performance characteristics of thin film resistors," https://www.susumu.co.jp/tech/know_how_03.php (4 pages), and English translation, https://www.susumu.eo.jp/english/tech/know_how_03.php (4 pages) visited Aug. 31, 2022.

* cited by examiner

*Primary Examiner* — Justin N Olamit
(74) *Attorney, Agent, or Firm* — Finnegan, Henderson, Farabow, Garrett & Dunner, LLP

(57) ABSTRACT

According to one embodiment, a sensor includes a first element including a first resistance member and a first conductive member, a second element including a second resistance member, and a third resistance member connected in series with the second resistance member. An absolute value of a third temperature coefficient of a third resistance of the third resistance member is smaller than an absolute value of a first temperature coefficient of a first resistance of the first resistance member. The absolute value of the third temperature coefficient is smaller than an absolute value of a second temperature coefficient of the second resistance member. The third resistance is lower than the second resistance.

17 Claims, 8 Drawing Sheets

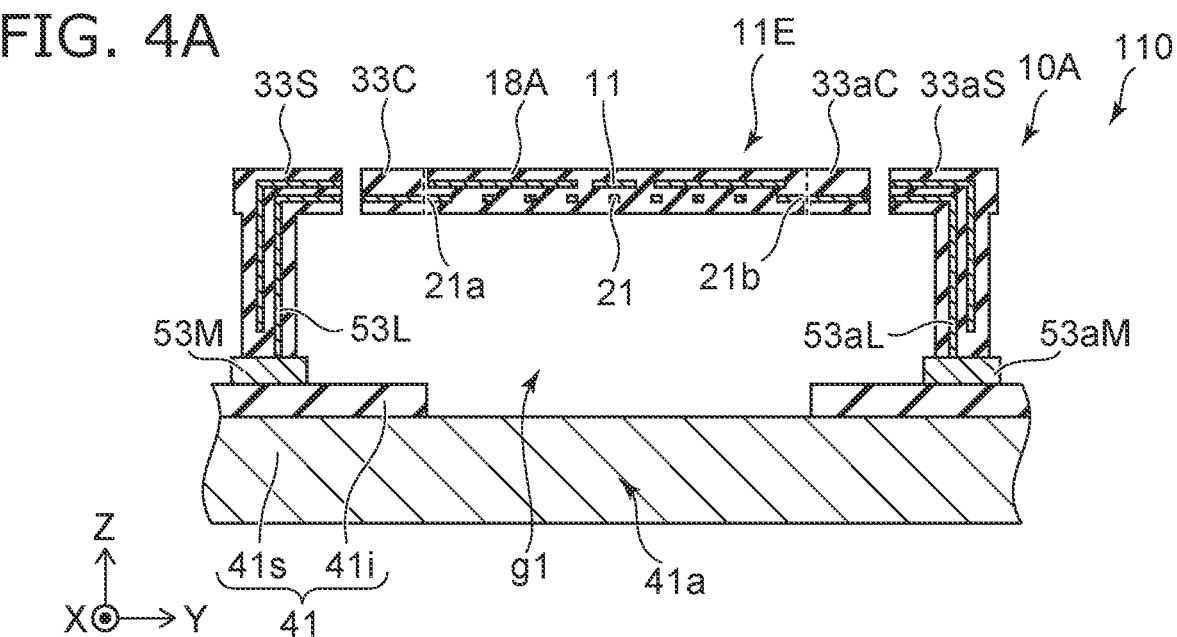
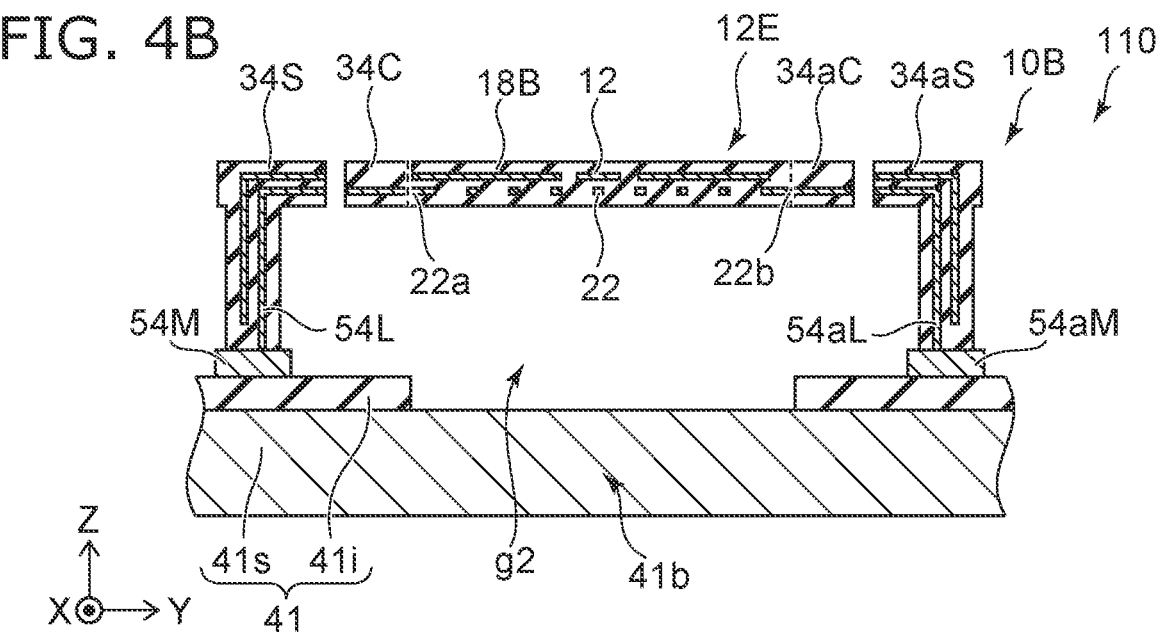

SENSOR

CROSS-REFERENCE TO RELATED APPLICATIONS

This application is based upon and claims the benefit of priority from Japanese Patent Application No. 2022-035782, filed on Mar. 9, 2022; the entire contents of which are incorporated herein by reference.

FIELD

Embodiments described herein relate generally to a sensor.

BACKGROUND

For example, there is a sensor based on a MEMS (Micro Electro Mechanical Systems) element or the like. It is desired to improve the accuracy of the sensor.

BRIEF DESCRIPTION OF THE DRAWINGS

FIGS. 4A and 4B are schematic cross-sectional views illustrating the sensor according to the first embodiment.

DETAILED DESCRIPTION

Figure 1:
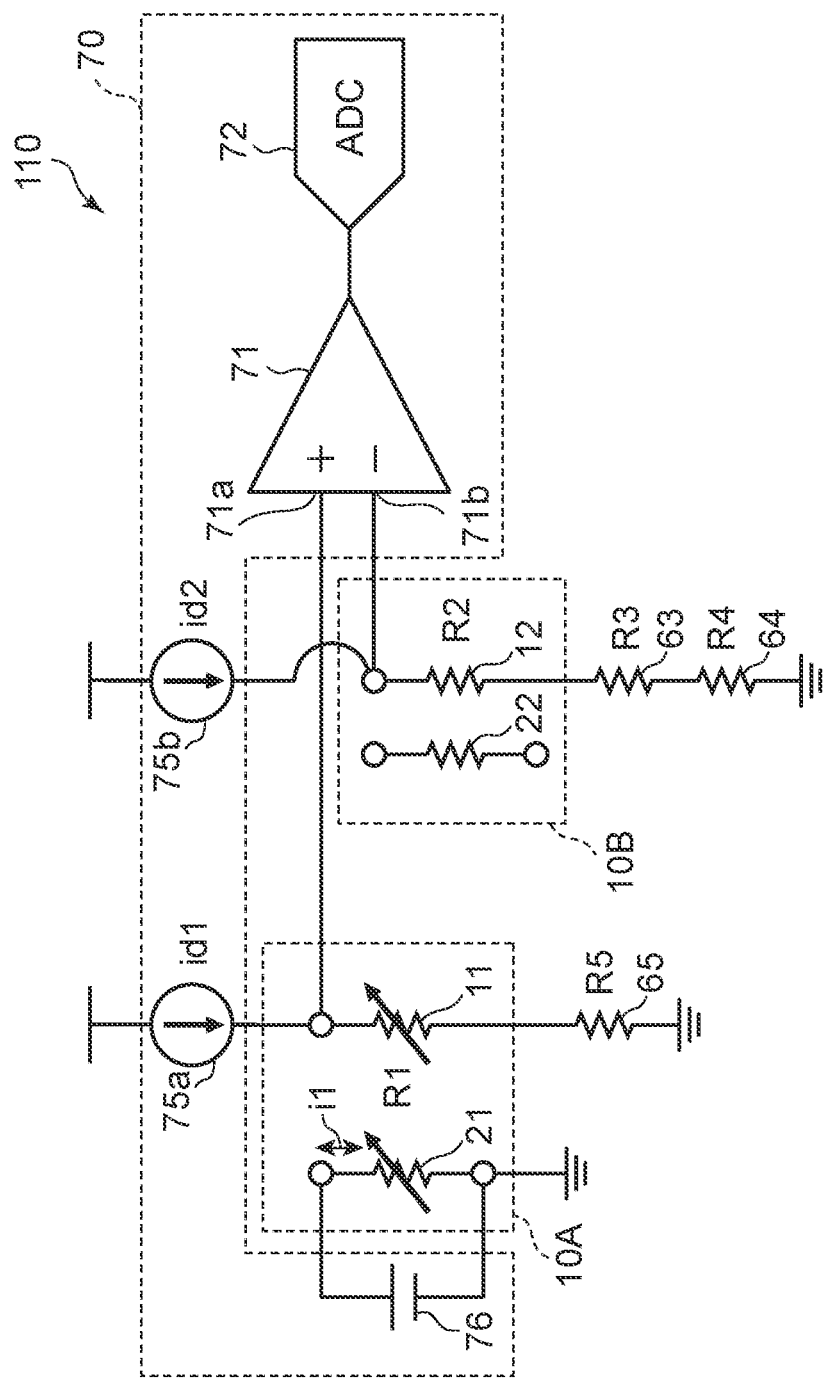
FIG. 1 is a schematic view illustrating a sensor according to a first embodiment.

According to one embodiment, a sensor includes a first element including a first resistance member and a first conductive member, a second element including a second resistance member, and a third resistance member connected in series with the second resistance member. An absolute value of a third temperature coefficient of a third resistance of the third resistance member is smaller than an absolute value of a first temperature coefficient of a first resistance of the first resistance member. The absolute value of the third temperature coefficient is smaller than an absolute value of a second temperature coefficient of the second resistance member. The third resistance is lower than the second resistance.

According to one embodiment, a sensor includes a first element including a first resistance member and a first conductive member, a second element including a second resistance member, and a third resistance member connected in parallel with the first resistance member. An absolute value of a third temperature coefficient of a third resistance of the third resistance member is smaller than an absolute value of a first temperature coefficient of a first resistance of the first resistance member.

Various embodiments are described below with reference to the accompanying drawings.

The drawings are schematic and conceptual; and the relationships between the thickness and width of portions, the proportions of sizes among portions, etc., are not necessarily the same as the actual values. The dimensions and proportions may be Illustrated differently among drawings, even for identical portions.

In the specification and drawings, components similar to those described previously or illustrated in an antecedent drawing are marked with like reference numerals, and a detailed description is omitted as appropriate.

First Embodiment

FIG. 1 is a schematic view illustrating a sensor according to a first embodiment.

FIG. 1 is a circuit diagram of a sensor 110 according to the embodiment. A shown in FIG. 1, the sensor 110 includes a first element 10A and a second element 10B.

The first element 10A includes a first resistance member 11 and a first conductive member 21. As described later, the first conductive member 21 functions as a heater. The second element 10B includes a second resistance member 12. In this example, the second element 10B includes a second conductive member 22. The second conductive member 22 is, for example, a dummy heater.

The sensor 110 further includes a third resistance member 63. The third resistance member 63 is connected in series with the second resistance member 12. The sensor 110 may include a wiring member 64 and a wiring member 65. The wiring member 64 is electrically connected with the second resistance member 12 and the third resistance member 63. The wiring member 65 is electrically connected with the first resistance member 11.

The first resistance member 11 has a first resistance R1. The second resistance member 12 has a second resistance R2. The third resistance member 63 has a third resistance R3. The wiring member 64 has a wiring resistance R4. The wiring member 65 has a wiring resistance R5. These resistances are electrical resistances.

In the embodiment, the absolute value of a third temperature coefficient of the third resistance R3 of the third resistance member 63 is smaller than the absolute value of a first temperature coefficient of the first resistance R1 of the first resistance member 11. The absolute value of the third temperature coefficient is smaller than the absolute value of a second temperature coefficient of the second resistance R2 of the second resistance member 12. The third resistance member 63 is a low temperature coefficient resistance.

The third resistance R3 of the third resistance member 63 is lower than the second resistance R2 of the second resistance member 12. For example, the wiring resistance R4 of the wiring member 64 is lower than the third resistance R3.

In the embodiment, for example, a current 11 is supplied to the first conductive member 21, For example, a power supply 76 applies a voltage to the first conductive member 21. As a result, the current 11 flows through the first conductive member 21. As the temperature of the first conductive member 21 rises, the temperature of the first resistance member 11 rises. At this time, the degree of heat conduction from the first resistance member 11 to the surrounding atmosphere changes depending on the type and concentration of the gas to be detected around the first element 10A, For example, the thermal conductivity of the surrounding atmosphere changes depending on the type of gas. For example, the thermal conductivity of the surrounding atmosphere changes depending on the concentration of the gas.

The degree of heating of the first resistance member 11 changes depending on the degree of heat conduction of the first resistance member 11. That is, the temperature of the first resistance member 11 changes according to the type and concentration of the gas to be detected. As a result, the electrical resistance of the first resistance member 11 changes. By detecting the change in the electrical resistance of the first resistance member 11, the type and concentration of the gas to be detected existing around the first element 10A can be detected.

In this example, a first detection current id1 is supplied to the first resistance member 11 from a first current source 75a. The potential of one end of the first resistance member 11 based on the first detection current id1 is detected.

On the other hand, the second element 10B is not provided with a conductive member. Alternatively, in the second element 10B, even if the conductive member (second conductive member 22) is provided, no current is supplied to the second conductive member 22. As a result, the temperature of the second resistance member 12 is substantially unaffected by the detection target. By observing the difference between the characteristics of the second resistance member 12 and the characteristics of the first resistance member 11, the change in temperature of the first resistance member 11 can be detected with high accuracy. As a result, the gas to be detected can be detected with high accuracy. The second resistance member 12 is, for example, a reference element.

For example, in the second element 10B, a second detection current id2 is supplied to the second resistance member 12 from a second current source 75b. The potential of the second resistance member 12 based on the second detection current id2 is detected.

In this example, a differential amplifier 71 is provided. The differential amplifier 71 includes a first input 71a and a second input 71b. A signal corresponding to the potential of the first resistance member 11 is input to the first input 71a. A signal corresponding to the potential of the second resistance member 12 is Input to the second input 71b.

By detecting a difference between the potential of the first resistance member 11 and the potential of the second resistance member 12, the change in the electric resistance of the first resistance member 11 due to the detection target can be extracted with high accuracy.

The output of the differential amplifier 71 may be input to an AD conversion circuit 72. The change in the electrical resistance of the first resistance member 11 may be output as a digital value.

The sensor 110 may include a circuit part 70. The circuit part 70 includes the differential amplifier 71. The circuit part 70 may include the AD conversion circuit 72. The circuit part 70 may include the power supply 76. The circuit part 70 may include the first current source 75a and the second current source 75b. The value of the second detection current id2 may be the same as the value of the first detection current id1.

For example, the configuration (material and shape) of the second resistance member 12 is substantially the same as the configuration (material and shape) of the first resistance member 11. As a result, when the temperatures of these resistance members are the same, the electrical resistance and the temperature coefficient of these resistance members are substantially the same. As a result, it is expected that the change in the resistance of the first resistance member 11 can be detected with high accuracy by differential amplification even when the environmental temperature around the sensor changes.

However, as described above, the first resistance member 11 is heated by the first conductive member 21. Therefore, in the detection operation, the temperature of the first resistance member 11 is higher than the temperature of the second resistance member 12. Therefore, a difference (offset) occurs between the electrical resistance of the first resistance member 11 and the electrical resistance of the second resistance member 12. This offset may result in inaccurate detection of changes in the resistance of the first resistance member 11. When the offset exceeds the operating range of the differential amplifier 71, it becomes difficult to detect the change in the resistance of the first resistance member 11.

On the other hand, a reference example for designing the second resistance member 12 can be considered in consideration of the change in the electric resistance due to the temperature rise of the first resistance member 11 in advance. For example, the shape of the second resistance member 12 is made different from the shape of the first resistance member 11. As a result, the electrical resistance of the second resistance member 12 whose temperature does not rise substantially can be made substantially the same as the electrical resistance of the first resistance member 11 whose temperature has risen. However, in this reference example, since the shape of the second resistance member 12 is different from the shape of the first resistance member 11, the temperature coefficients of the electrical resistance of these resistance members do not match. There is a difference in temperature coefficient. Therefore, for example, when the environmental temperature around the sensor changes, it is difficult to detect the change in the electrical resistance of the first resistance member 11 with high accuracy.

In the embodiment, the third resistance member 63 is provided. The third resistance member 63 is connected in series with the second resistance member 12. As a result, the electrical resistance of the series circuit of the second resistance member 12 and the third resistance member 63 increases. The electrical resistance of the series circuit can be made substantially the same as the electrical resistance of the first resistance member 11 when the temperature rises.

Further, the third resistance member 63 is set to have a small temperature coefficient of electrical resistance. For example, as will be described later, a material of the third resistance member 63 is different from that of the first resistance member 11 and the second resistance member 12. As a result, a low temperature coefficient can be obtained in the third resistance member 63.

Since the temperature coefficient of the third resistance member 63 is small, the temperature change of the electrical resistance of the third resistance member 63 can be substantially ignored. As a result, a difference in temperature coefficient between the series circuit including the second resistance member 12 and the third resistance member 63 and the first resistance member 11 can be made small to a negligible extent. The difference in temperature coefficient can be suppressed.

In the embodiment, the change in the electric resistance of the first resistance member 11 can be detected with high accuracy even when the environmental temperature around the sensor changes, for example. As a result, the detection target can be detected with high accuracy in a wide temperature range.

For example, the first resistance member 11 is heated by the first conductive member 21. A material that can obtain stable characteristics even when heated is applied to the first resistance member 11. The temperature coefficient is not always small in materials that emphasize stability of properties. In other words, the temperature coefficient of the first resistance member 11 is relatively large.

As described above, the second resistance member 12 is a reference element. Therefore, it is preferable that the configuration of the second resistance member 12 is set to be substantially the same as the configuration of the first resistance member 11. Therefore, the temperature characteristic of the second resistance member 12 is also large as in the first resistance member 11.

In the embodiment, by providing the third resistance member 63, the configuration of the second resistance member 12 can be the same as the configuration of the first resistance member 11. Thereby, for example, the temperature coefficient of the second resistance member 12 can be made substantially the same as the temperature coefficient of the first resistance member 11. For example, the design of the second resistance member 12 is simplified and the manufacturing efficiency is high.

As described above, in the embodiment, the absolute value of the third temperature coefficient of the third resistance R3 of the third resistance member 63 is smaller than the absolute value of the first temperature coefficient of the first resistance R1 of the first resistance member 11. The absolute value of the third temperature coefficient is smaller than the absolute value of the second temperature coefficient of the second resistance R2 of the second resistance member 12. The third resistance member 63 having a small temperature coefficient is used. Thereby, the electrical resistance of the series circuit including the second element 10B and the third resistance member 63 can be made substantially the same as the resistance of the first element 10A when heated. Then, the temperature coefficient of the series circuit can be made substantially the same as the temperature coefficient of the first element 10A.

In the embodiment, the third resistance R3 is lower than the second resistance R2. The sum of the third resistance R3 and the second resistance R2 is substantially the same as the first resistance R1 when heated. For example, the third resistance R3 corresponds to a difference between the first resistance R1 when heated and the second resistance R2 which is substantially unheated. The amount of change in the first resistance R1 due to the temperature change of the first resistance member 11 is smaller than the absolute value of the first resistance R1 (that is, the absolute value of the second resistance R2). Since the third resistance R3 is lower than the second resistance R2, the sum of the third resistance R3 and the second resistance R2 can be substantially the same as the first resistance R1 when heated. In the embodiment, the third resistance R3 is lower than the first resistance R1.

A wiring resistance exists in the first element 10A and the second element 10B. The wiring resistance is lower than the resistance of the resistance member. As a result, the desired operation can be obtained while suppressing the loss.

For example, in the first element 10A, there is a wiring resistance (not shown in FIG. 1) due to the wiring member. This wiring resistance is lower than that of the first resistance R1 of the first resistance member 11, and can be ignored.

For example, in the second element 10B, there is a wiring resistance R4 due to the wiring member 64, The wiring resistance R4 is lower than the second resistance R2 of the second resistance member 12, and lower than the third resistance R3 of the third resistance member 63.

In the embodiment, the absolute value of the third temperature coefficient of the third resistance R3 of the third resistance member 63 is not more than ⅓ of the absolute value of the first temperature coefficient of the first resistance R1 of the first resistance member. The absolute value of the third temperature coefficient is not more than ⅓ of the absolute value of the second temperature coefficient of the second resistance R2 of the second resistance member 12. This makes it possible to suppress the difference in temperature coefficient.

In the embodiment, the absolute value of the first temperature coefficient is, for example, not less than 300 ppm/K. The absolute value of the second temperature coefficient is, for example, not less than 300 ppm/K. The absolute value of the third temperature coefficient is, for example, not more than 100 ppm/K. The absolute value of the third temperature coefficient may be, for example, not more than 50 ppm/K. The difference in temperature coefficient can be further suppressed.

For example, the third resistance member 63 includes, for example, at least one selected from the group consisting of Ni and Cr. A small temperature coefficient is obtained. For example, the third resistance member 63 includes Ni and Cr. At this time, the composition ratio of Cr in the third resistance member 63 is, for example, not less than 30 wt % and not more than 80 wt %. An example of the temperature coefficient of a material including Ni and Cr will be described later.

The first resistance member 11 and the second resistance member 12 include at least one selected from the group consisting of TI, TiN, Al, W, Si, Cu, Au, Pd and Pt. For example, in the first resistance member 11, stable characteristics can be obtained when heated. The material of the second resistance member 12 is, for example, the same as the material of the first resistance member 11. In the second resistance member 12, good characteristics as a reference element can be obtained.

The wiring member 64 includes, for example, at least one selected from the group consisting of aluminum, copper and gold. Low wiring resistance R4 is stable and easy to obtain.

The wiring resistance R4 is, for example, not more than ⅓ times of the third resistance R3. The wiring resistance R4 is, for example, not less than 0.01Ω and less than 100Ω. The wiring resistance R5 is, for example, not more than ⅓ times of the first resistance R1. The wiring resistance R5 is, for example, not less than 0.01Ω and less than 100Ω. The third resistance R3 is, for example, not less than 2Ω and not more than 100 kΩ. The first resistance R1 is, for example, not less than 100Ω and not more than 1 MΩ. The second resistance R2 is, for example, not less than 100Ω and not more than 1 MΩ.

Figure 2:
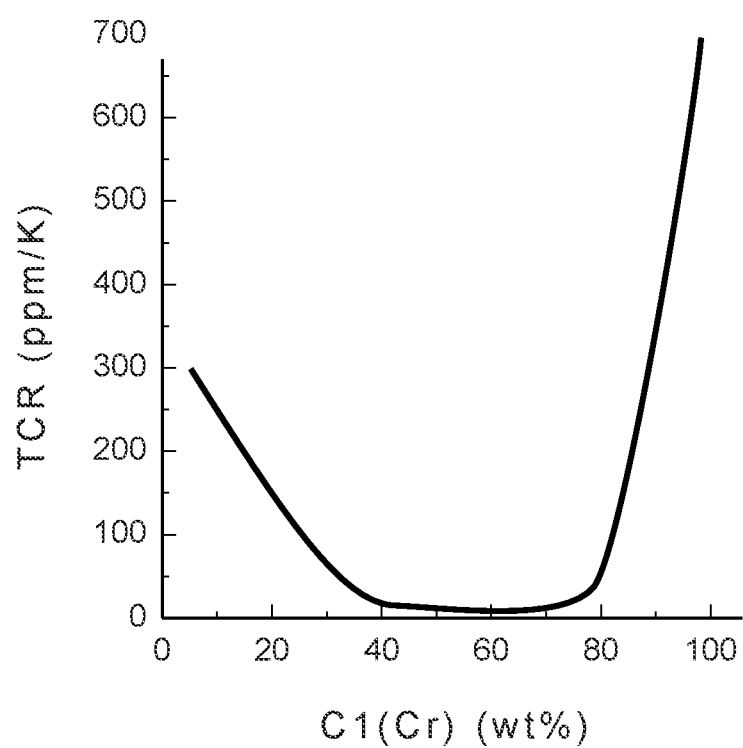
FIG. 2 is a graph illustrating characteristics of the sensor.

FIG. 2 is a graph Illustrating characteristics of the sensor.

FIG. 2 illustrates a temperature coefficient of a material including Ni and Cr. The horizontal axis is a concentration C1 (Cr) of Cr. The vertical axis is a temperature coefficient TCR of electrical resistivity. As shown in FIG. 2, a small temperature coefficient TCR can be obtained when the Cr concentration C1 (Cr) is not less than 30 wt % and not more than 80 wt %. When the third resistance member 63 includes Ni and Cr, the composition ratio of Cr in the third resistance member 63 is preferably, for example, not less than 30 wt % and not more than 80 wt %. When the third resistance member 63 includes Ni and Cr, the composition ratio of Cr in the third resistance member 63 is more preferably not less than 40 wt % and not more than 80 wt %, for example. An even smaller temperature coefficient TCR is obtained.

In the following, an example of the configuration of the first element 10A and the second element 10B will be described.

Figure 3:
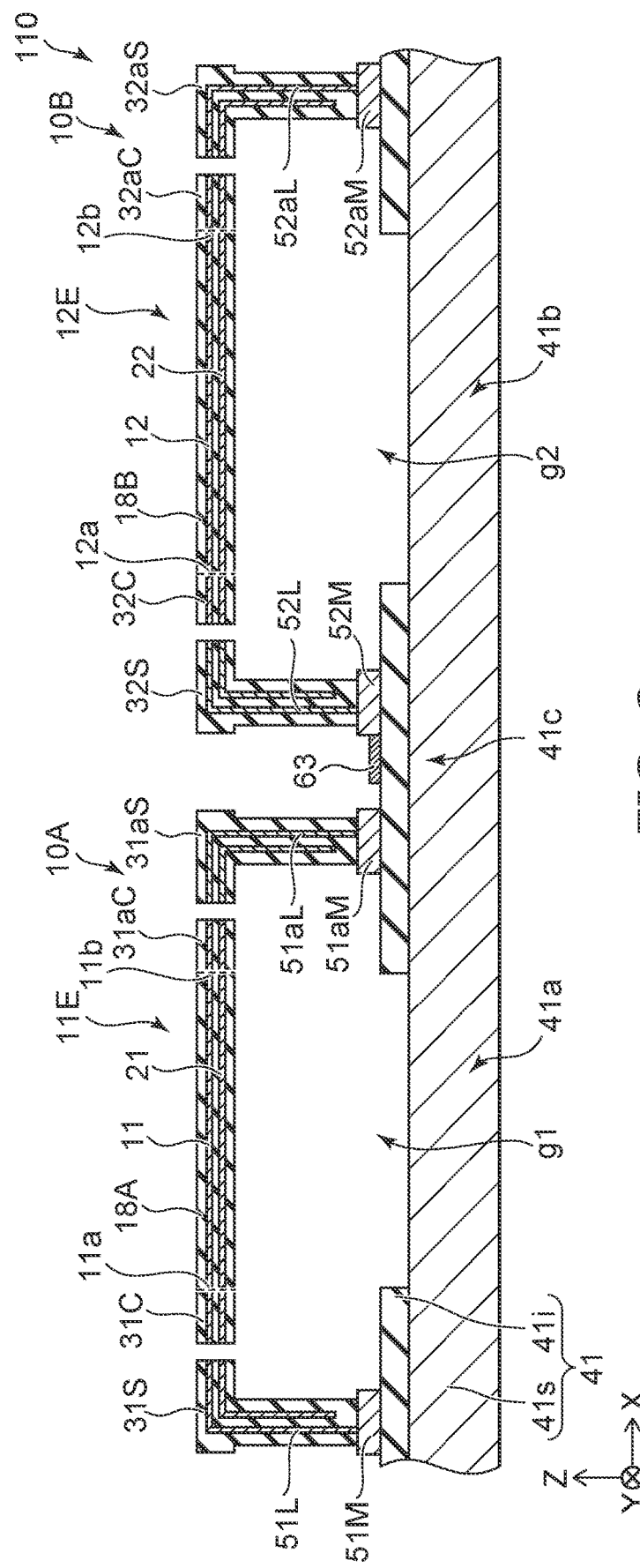
FIG. 3 is a schematic cross-sectional view Illustrating the sensor according to the first embodiment.

FIGS. 3, 4A and 48 are schematic cross-sectional views illustrating the sensor according to the first embodiment.

Figure 5:
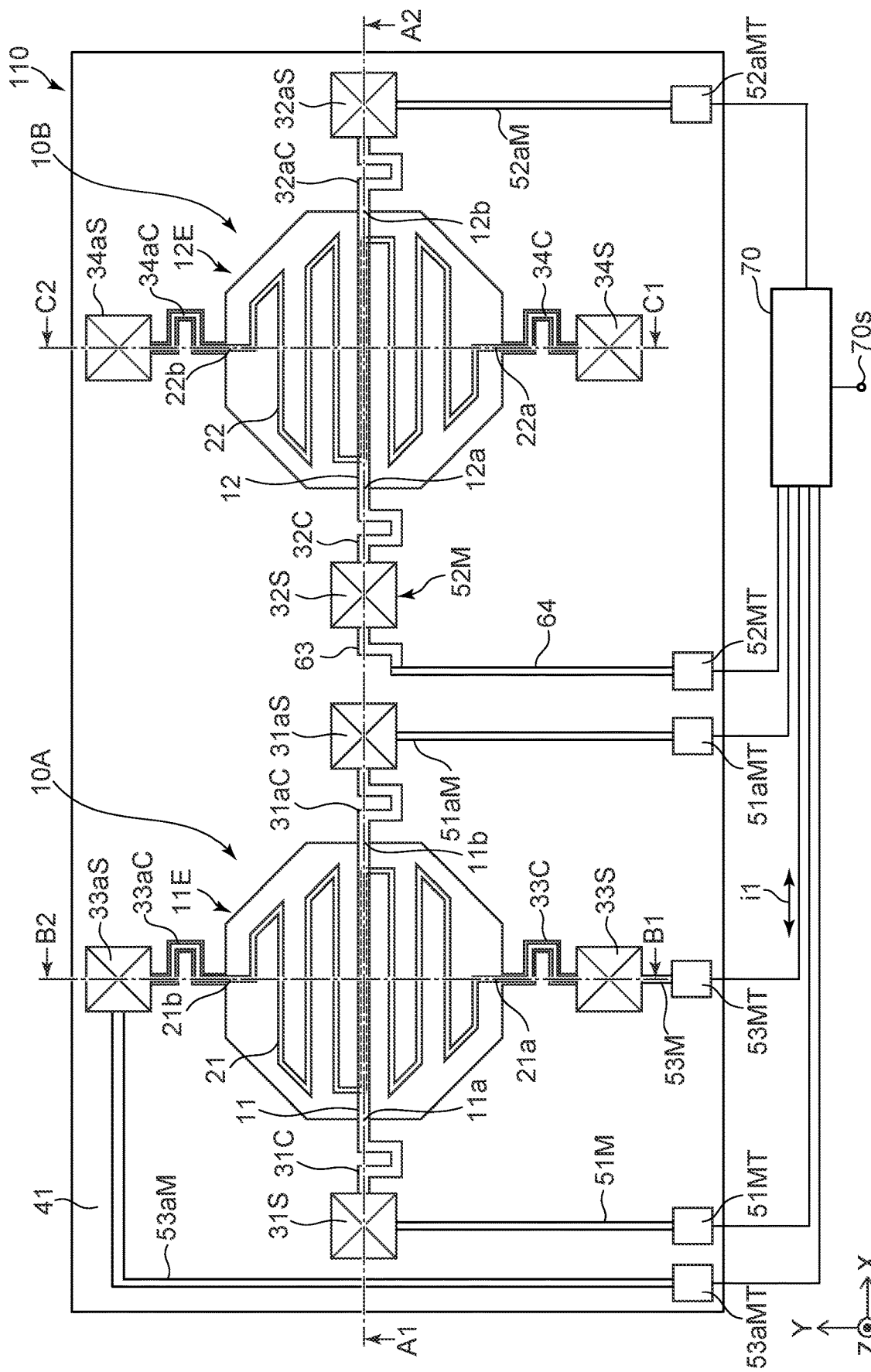
FIG. 5 is a schematic plan view illustrating the sensor according to the first embodiment.

FIG. 5 is a schematic plan view illustrating the sensor according to the first embodiment.

FIG. 3 is a cross-sectional view taken along line A1-A2 of FIG. 5. FIG. 4A is a cross-sectional view taken along line B1-B2 of FIG. 5. FIG. 4B is a cross-sectional view taken along line C1-C2 of FIG. 5.

As shown in FIGS. 3, 4A, 4B and 5, the sensor 110 according to the embodiment includes a base body 41, the first element 10A, the second element 10B, the third resistance member 63 and the wiring member 64.

The base body 41 includes a first base body region 41a and a second base body region 41b. In this example, the base body 41 includes a substrate 41s and an insulating film 41i. The substrate 41s may be, for example, a semiconductor substrate (for example, a silicon substrate). The substrate 41s may include, for example, a semiconductor circuit or the like. The substrate 41s may include a connecting member such as a via electrode.

The first element 10A is provided in the first base body region 41a. A first direction from the first base body region 41a to the first element 10A is taken as a Z-axis direction. One direction perpendicular to the Z-axis direction is taken as an X-axis direction. A direction perpendicular to the Z-axis direction and the X-axis direction is taken as a Y-axis direction.

A second direction from the first base body region 41a to the second base body region 41b crosses the first direction. The second direction is, for example, the X-axis direction.

The first element 10A includes a first detection element 11E. The first detection element 11E includes the first resistance member 11 and the first conductive member 21. As shown in FIGS. 3 and 5, the first resistance member 11 includes a first resistance portion 11a and a first resistance other portion 11b. For example, the first resistance portion 11a may be one end of the first resistance member 11. The first resistance other portion 11b may be another end of the first resistance member 11. As shown in FIGS. 4A and 5, the first conductive member 21 includes a first conductive portion 21a and a first conductive other portion 21b. For example, the first conductive portion 21a may be one end of the first conductive member 21. The first conductive other portion 21b may be another end of the first conductive member 21.

As shown in FIGS. 3 and 5, in this example, the first element 10A further includes a first connection portion 31C and a first support portion 31S. The first support portion 31S is fixed to the base body 41. A part of the first connection portion 31C is supported by the first support portion 31S. Another part of the first connection portion 31C supports the first detection element 11E away from the first base body region 41a. A first gap g1 is provided between the first base body region 41a and the first detection element 11E.

In this example, the first element 10A further includes a first other connection portion 31aC and a first other support portion 31aS. The first other support portion 31aS is fixed to the base body 41. A part of the first other connection portion 31aC is supported by the first other support portion 31aS. Another part of the first other connection portion 31aC supports the first detection element 11E away from the first base body region 41a. In this example, there is at least a part of the first detection element 11E between the first connection portion 31C and the first other connection portion 31aC.

The second element 10B is provided in the second base body region 41b. A direction from the second base body region 41b to the second element 10B is along the Z-axis direction.

The second element 10B includes a second detection element 12E. In this example, the second detection element 12E includes the second resistance member 12 and the second conductive member 22. As shown in FIGS. 3 and 5, the second resistance member 12 includes a second resistance portion 12a and a second resistance other portion 12b. For example, the second resistance portion 12a may be one end of the second resistance member 12. The second resistance other portion 12b may be another end of the second resistance member 12. As shown in FIGS. 4B and 5, the second conductive member 22 includes a second conductive portion 22a and a second conductive other portion 22b, For example, the second conductive portion 22a may be one end of the second conductive member 22. The second conductive other portion 22b may be another end of the second conductive member 22.

As shown in FIGS. 3 and 5, in this example, the second element 10B further includes a second connection portion 32C and a second support portion 32S. The second support portion 32S is fixed to the base body 41. A part of the second connection portion 32C is supported by the second support portion 32S. Another part of the second connection portion 32C supports the second detection element 12E away from the second base body region 41b. In this example, the second gap g2 is provided between the second base body region 41b and the second detection element 12E.

In this example, the second element 10B further includes a second other connection portion 32aC and a second other support portion 32aS. The second other support portion 32aS is fixed to the base body 41. A part of the second other connection portion 32aC is supported by the second other support portion 32aS. Another part of the second other connection portion 32aC supports the second detection element 12E away from the second base body region 41b. In this example, there is at least a part of the second detection element 12E between the second connection portion 32C and the second other connection portion 32aC.

By supporting the first detection element 11E away from the base body 41, the heat of these detection elements is suppressed from being conducted through the base body 41. This facilitates stable detection of the detection target with high sensitivity.

For example, the first resistance portion 11a is electrically connected with the circuit part 70 via a wiring layer 51M and a terminal 51MT. For example, the first resistance other portion 11b is electrically connected with the circuit part 70 via a wiring layer 51aM and a terminal 51aMT, For example, the first conductive portion 21a is electrically connected with the circuit part 70 via a wiring layer 53M and a terminal 53MT. For example, the first conductive other portion 21b is electrically connected with the circuit part 70 via the wiring layer 53aM and the terminal 53aMT.

For example, the second resistance portion 12a is electrically connected with the third resistance member 63 via a wiring layer 52M. The third resistance member 63 is electrically connected with the wiring member 64. The wiring member 64 is electrically connected with the circuit part 70 via a terminal 52MT. For example, the second resistance other portion 12b is electrically connected with the circuit part 70 via a wiring layer 52aM and a terminal 52aMT. The second conductive portion 22a is not electrically connected with the circuit part 70. The second conductive other portion 22b is not electrically connected with the circuit part 70. In the embodiment, the second conductive portion 22a and the second conductive other portion 22b may be electrically connected with the circuit part 70, and no current may be supplied from the circuit part 70.

The circuit part 70 outputs a signal 70s corresponding to the output of the differential amplifier 71 (see FIG. 1).

As shown in FIG. 3, the first element 10A (and the first detection element 11E) may include a first insulating member 18A. The second element 10B (and the second detection element 12E) may include a second insulating member 18B. At least a part of the first insulating member 18A is provided around the first resistance member 11 and the first conductive member 21, A part of the first insulating member 18A is provided between the first resistance member 11 and the first conductive member 21. At least a part of the second insulating member 18B is provided around the second resistance member 12 and the second conductive member 22. A part of the second insulating member 18B is provided between the second resistance member 12 and the second conductive member 22. The second insulating member 18B has substantially the same structure as the first insulating member 18A. A length, width, thickness and material of the second insulating member 18B are substantially the same as a length, width, thickness and material of the first insulating member 18A.

As shown in FIG. 3, the first element 10A may further include a first conductive layer 51L. The first conductive layer 51L is electrically connected with the first resistance portion 11a of the first resistance member 11. At least a part of the first conductive layer 51L may be provided on the first support portion 31S. In this example, the first conductive layer 51L Is electrically connected with the wiring layer 51M provided on the base body 41.

As shown in FIG. 3, the second element 10B may further include a second conductive layer 52L. The second conductive layer 52L is electrically connected with the second resistance portion 12a of the second resistance member 12. At least a part of the second conductive layer 52L may be provided on the second support portion 32S. In this example, the second conductive layer 52L is electrically connected with the wiring layer 52M provided on the base body 41.

The first element 10A may further include a first other conductive layer 51aL. The first other conductive layer 51aL is electrically connected with the first resistance other portion 11b of the first resistance member 11. At least a part of the first other conductive layer 51al may be provided on the first other support portion 31aS. In this example, the first other conductive layer 51aL is electrically connected with the wiring layer 51aM provided on the base body 41.

The second element 10B may further include a second other conductive layer 52aL. The second other conductive layer 52aL is electrically connected with the second resistance other portion 12b of the second resistance member 12. At least a part of the second other conductive layer 52aL may be provided on the second other support portion 32aS. In this example, the second other conductive layer 52al is electrically connected with the wiring layer 52aM provided on the base body 41.

As shown in FIGS. 4A and 5, in this example, the first element 10A includes a third connection portion 33C and a third support portion 33S. The third support portion 33S is fixed to the base body 41. A part of the third connection portion 33C is supported by the third support portion 33S. Another part of the third connection portion 33C supports the first detection element 11E away from the first base body region 41a.

In this example, the first element 10A includes a third other connection portion 33aC and a third other support portion 33aS. The third other support portion 33aS is fixed to the base body 41. A part of the third other connection portion 33aC is supported by the third other support portion 33aS. Another part of the third other connection portion 33aC supports the first detection element 11E away from the first base body region 41a.

As shown in FIG. 4A, the first element 10A may further include a third conductive layer 53L. At least a part of the third conductive layer 53L is provided on the third support portion 33S. In this example, the third conductive layer 53L is electrically connected with the wiring layer 53M provided on the base body 41.

As shown in FIG. 4A, the first element 10A may further include a third other conductive layer 53aL. At least a part of the third other conductive layer 53aL is provided on the third other support portion 33aS. In this example, the third other conductive layer 53al is electrically connected with the wiring layer 53aM provided on the base body 41.

As shown in FIGS. 4B and 5, in this example, the second element 10B includes a fourth connection portion 34C and a fourth support portion 34S. The fourth support portion 34S is fixed to the base body 41. A part of the fourth connection portion 34C is supported by the fourth support portion 34S. Another portion of the fourth connection portion 34C supports the second detection element 12E away from the second base body region 41b.

In this example, the second element 10B includes a fourth other connection portion 34aC and a fourth other support portion 34aS. The fourth other support portion 34aS is fixed to the base body 41. A part of the fourth other connecting portion 34aC is supported by the fourth other support portion 34aS. Another part of the fourth other connection portion 34aC supports the second detection element 12E away from the second base body region 41b.

As shown in FIG. 4B, the second element 10B may further include a fourth conductive layer 54L. At least a part of the fourth conductive layer 54L is provided on the fourth support portion 34S. In this example, the fourth conductive layer 54L is electrically connected with the wiring layer 54M provided on the base body 41. The fourth conductive layer 54L is electrically connected with the second conductive portion 22a.

As shown in FIG. 4B, the second element 10B may further Include a fourth other conductive layer 54aL. At least a part of the fourth other conductive layer 54al is provided on the fourth other support portion 34aS. In this example, the fourth other conductive layer 54al is electrically connected with the wiring layer 54aM provided on the base body 41. The fourth other conductive layer 54al is electrically connected with the second conductive other portion 22b.

Figure 6A:
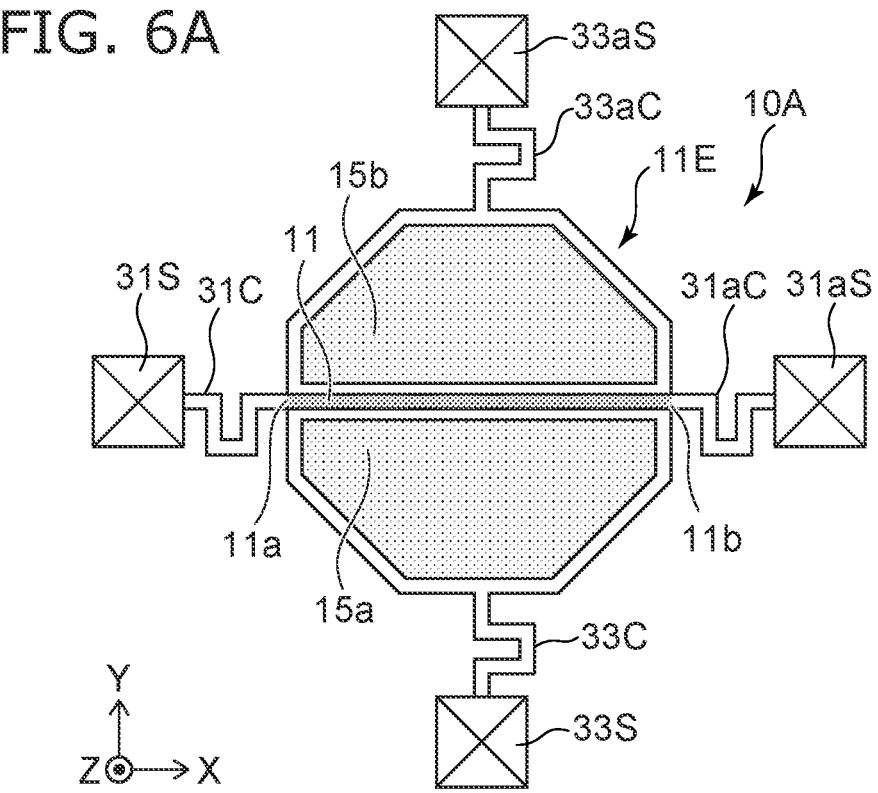
FIGS. 6A and 6B are schematic plan views illustrating the sensor according to the first embodiment.
Figure 6B:
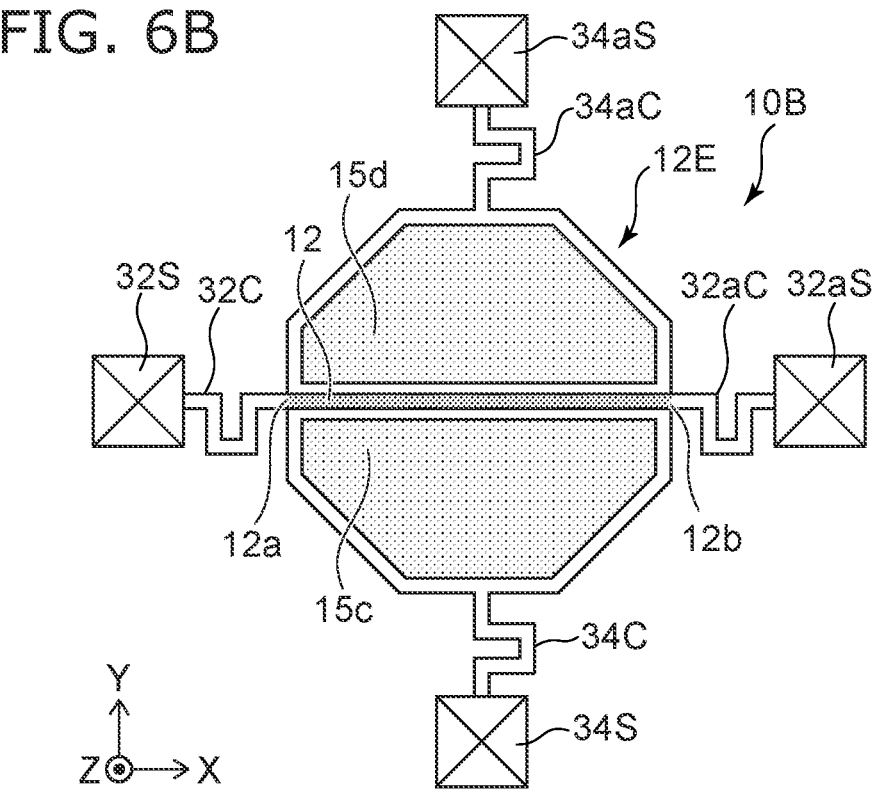

FIGS. 6A and 6B are schematic plan views illustrating the sensor according to the first embodiment.

These figures are plan views of the layer including the first resistance member 11 and the second resistance member 12.

As shown in FIG. 6A, the first detection element 11E may include a first layer 15a and a second layer 15b. The first layer 15a and the second layer 15b have the same material and thickness as the first resistance member 11. The first resistance member 11 is provided between the first layer 15a and the second layer 15b. By providing these layers, warp (deformation) of the first detection element 11E is suppressed.

As shown in FIG. 6B, the second detection element 12E may Include a third layer 15c and a fourth layer 15d. The third layer 15c and the fourth layer 15d have the same material and thickness as the second resistance member 12. The second resistance member 12 is provided between the third layer 15c and the fourth layer 15d. By providing these layers, warp (deformation) of the second detection element 12E is suppressed.

As described above, in this example, the first gap g1 is provided between the first base body region 41a and the first resistance member 11, and the second gap g2 is provided between the second base body region 41b and the second resistance member 12. In the embodiment, it is not necessary to provide a gap between the second base body region 41b and the second resistance member 12.

As shown in FIG. 5, a position of the third resistance member 63 in the second direction (for example, the X-axis direction) is between a position of the first resistance member 11 in the second direction and a position of the second resistance member 12 in the second direction. The second resistance member 12 is provided at a position far from the first resistance member 11. In the second resistance member 12, the influence of the temperature rise of the first element 10A is suppressed. Even if the third resistance member 63 having a small temperature coefficient is provided near the first resistance member 11 (first element 10A), the influence of the temperature rise on the third resistance member 63 can be substantially ignored.

As shown in FIG. 3, the base body 41 may include a third base body region 41c. The third base body region 41c is between the first base body region 41a and the second base body region 41b. The third resistance member 63 is provided, for example, in the third base body region 41c.

For example, the planar shape of the second element 10B in the plane (X-Y plane) crossing the first direction (Z-axis direction) is substantially the same as the planar shape of the first element 10A in the plane (X-Y plane).

Second Embodiment

Figure 7:
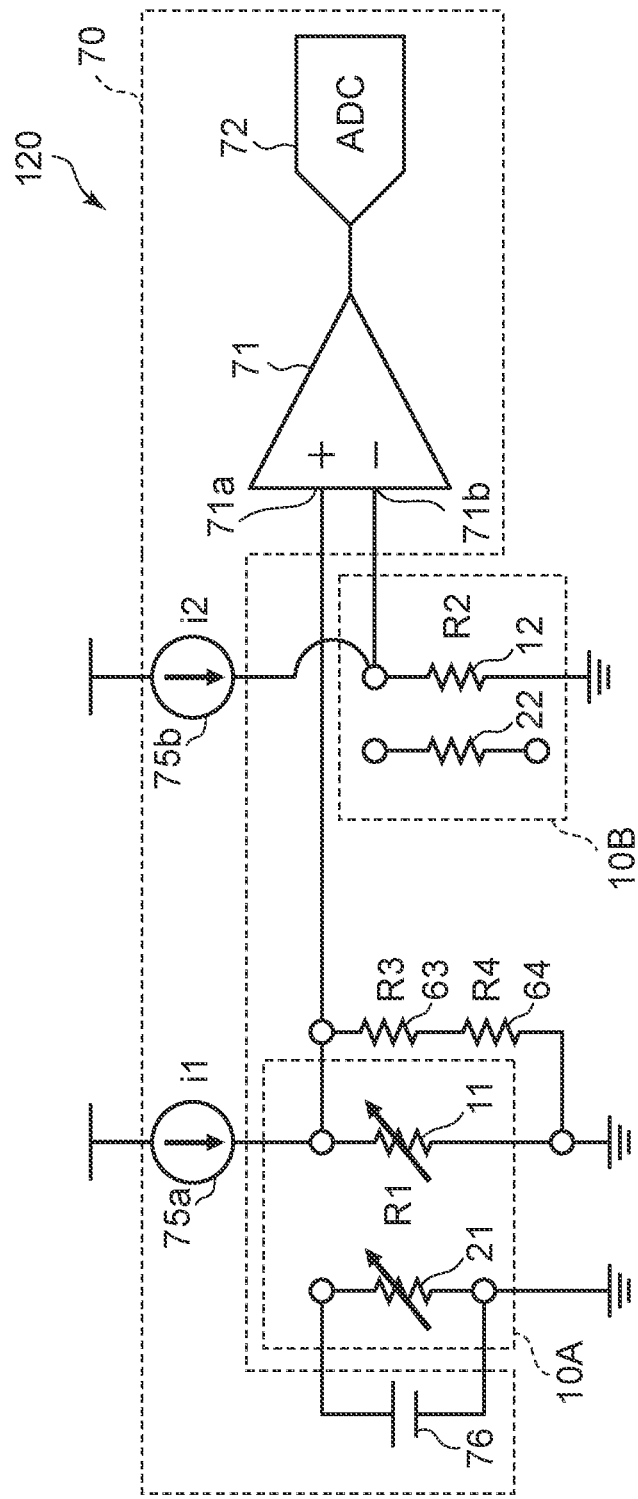
FIG. 7 is a schematic view illustrating a sensor according to a second embodiment.

FIG. 7 is a schematic view illustrating a sensor according to a second embodiment.

FIG. 7 is a circuit diagram of a sensor 120 according to the embodiment. As shown in FIG. 7, the sensor 120 includes the first element 10A, the second element 10B, and the third resistance member 63.

The first element 10A includes the first resistance member 11 and the first conductive member 21. The second element 10B includes the second resistance member 12. The second element 10B may include the second conductive member 22. The third resistance member 63 is connected in parallel with the first resistance member 11. The absolute value of the third temperature coefficient of the third resistance R3 of the third resistance member 63 is smaller than the absolute value of the first temperature coefficient of the first resistance R1 of the first resistance member 11. In the sensor 120, the configuration of the first element 10A and the second element 10B may be the same as the configuration of the sensor 110.

In the sensor 120, a parallel circuit including the first resistance member 11 and the third resistance member 63 is provided. As a result, when the temperature of the first resistance member 11 rises, the electrical resistance of the parallel circuit approaches the electrical resistance of the second resistance member 12. Since the absolute value of the third temperature coefficient of the third resistance R3 of the third resistance member 63 is small, the temperature coefficient of the parallel circuit can be made substantially the same as the temperature coefficient of the second element 10B.

In this example, the wiring member 64 is connected in series with the third resistance member 63. The third resistance member 63 and the wiring member 64 connected in series are connected in parallel with the first resistance member 11. The wiring resistance R4 of the wiring member 64 is lower than the third resistance R3. The wiring resistance R4 may be practically ignored.

Figure 8:
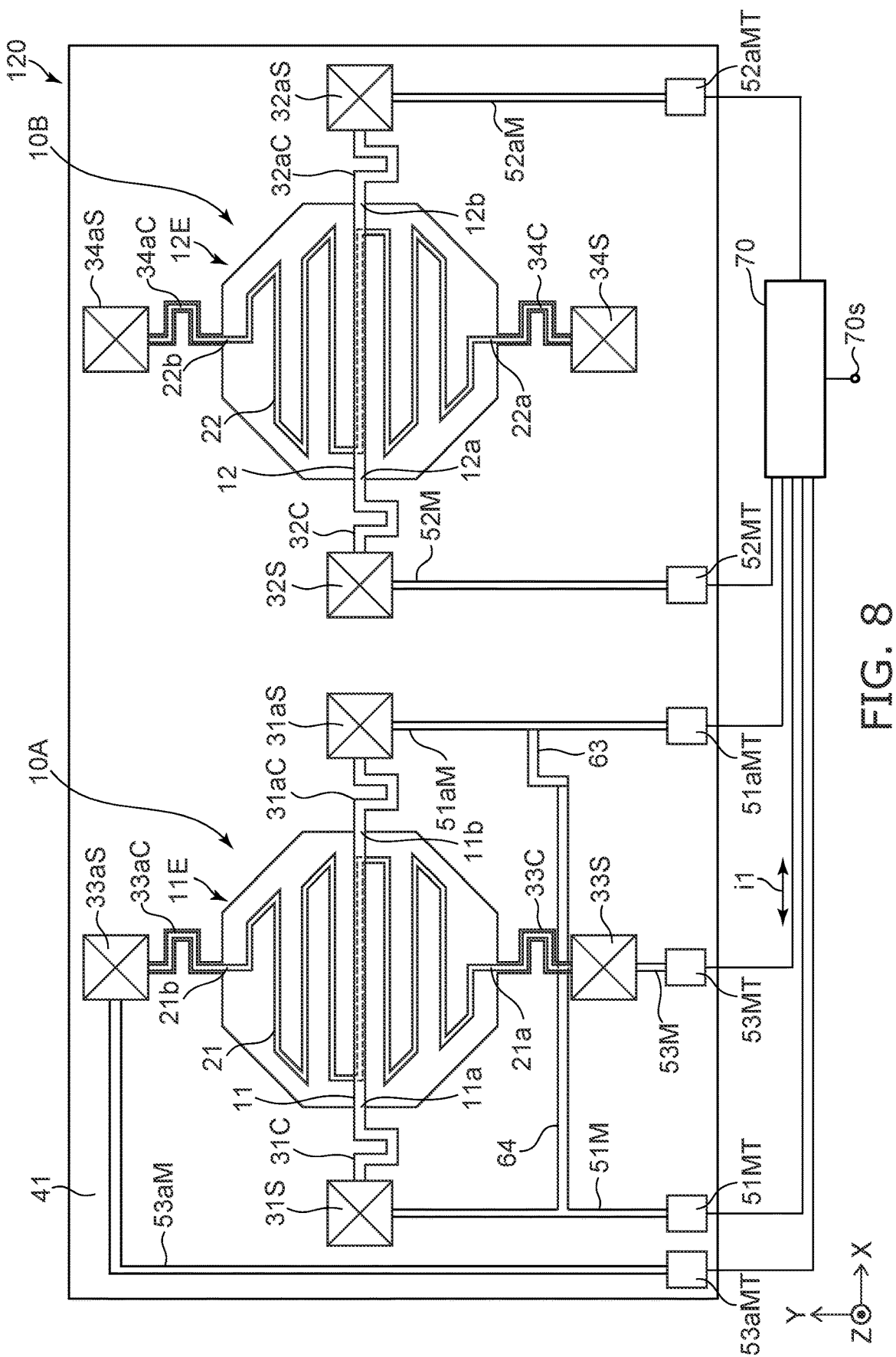
FIG. 8 is a schematic plan view illustrating the sensor according to the second embodiment.

FIG. 8 is a schematic plan view Illustrating the sensor according to the second embodiment.

As shown in FIG. 8, in the sensor 120 according to the embodiment, the third resistance member 63 is provided. The third resistance member 63 is electrically connected in parallel with the first resistance portion 11a and the first resistance other portion 11b. In this example, the wiring member 64 electrically connected with the third resistance member 63 makes an electrical connection. In this example, the wiring member 64 crosses the first element 10A (for example, the third connection portion 33C) in the Z-axis direction. The wiring member 64 may be a bonding wire.

In the first embodiment and the second embodiment, the first resistance R1 of the first resistance member 11 changes due to the temperature rise of the first resistance member 11 due to the current I1 flowing through the first conductive member 21. A third resistance member 63 is provided to compensate for the changed resistance. As a result, the detection target can be detected with high accuracy. The first resistance R1 changed due to the temperature rise changes according to the state of the gas (detection target) around the first element 10A.

In embodiments, detection targets include, for example, at least one selected from the group consisting of hydrogen, helium, carbon dioxide, methane and sulfur hexafluoride ($SF_6$), methane and propane.

In the embodiment, the operation of the sensor may be linked with the arithmetic device. For example, data of an appropriate value regarding the resistance value of the third resistance member 63 from the test result of the sensor may be stored in the memory. Using the test results after manufacturing the sensor, the shape of the resistance layer to be the third resistance member 63 may be deformed by trimming or the like. In the third resistance member 63, the resistance is adjusted. Trimming may be performed using, for example, a laser.

The embodiment may include the following configurations (e.g., technical proposals).

Configuration 1

A sensor, comprising:
   a first element including a first resistance member and a first conductive member;
   a second element including a second resistance member; and
   a third resistance member connected in series with the second resistance member,
   an absolute value of a third temperature coefficient of a third resistance of the third resistance member being smaller than an absolute value of a first temperature coefficient of a first resistance of the first resistance member,
   the absolute value of the third temperature coefficient being smaller than an absolute value of a second temperature coefficient of the second resistance member, and
   the third resistance being lower than the second resistance, Configuration 2

The sensor according to Configuration 1, wherein the third resistance is lower than the first resistance.

Configuration 3

The sensor according to Configuration 1 or 2, further comprising:
   a wiring member electrically connected with the second resistance member and the third resistance member, a wiring resistance of the wiring member being lower than the third resistance.

Configuration 4

A sensor, comprising:
a first element including a first resistance member and a first conductive member;
a second element including a second resistance member; and
a third resistance member connected in parallel with the first resistance member,
an absolute value of a third temperature coefficient of a third resistance of the third resistance member being smaller than an absolute value of a first temperature coefficient of a first resistance of the first resistance member.

Configuration 5

The sensor according to Configuration 4, further comprising:
a wiring member connected in series with the third resistance member,
the third resistance member and the wiring member connected in series being connected in parallel with the first resistance member,
a wiring resistance of the wiring member being lower than the third resistance.

Configuration 6

The sensor according to Configuration 1 or 4, wherein
a first resistance of the first resistance member changes due to temperature rise of the first resistance member due to a current flowing through the first conductive member.

Configuration 7

The sensor according to Configuration 6, wherein
the first resistance changed due to the temperature rise changes depending on a state of gas around the first element.

Configuration 8

The sensor according to any one of Configurations 1 to 7, wherein
the second element further includes a second conductive member.

Configuration 9

The sensor according to any one of Configurations 1 to 8, further comprising:
a base body including a first base body region and a second base body region,
the first element being provided in the first base body region,
a first gap being provided between the first base body region and the first resistance member,
the second element being provided in the second base body region, and
a second direction from the first base body region to the second base body region crossing a first direction from the first base body region to the first resistance member.

Configuration 10

The sensor according to Configuration 9, wherein
a second gap is provided between the second base body region and the second resistance member.

Configuration 11

The sensor according to Configuration 9 or 10, wherein
a planar shape of the second element in a plane crossing the first direction is substantially same as a planar shape of the first element in the plane, Configuration 12

The sensor according to any one of Configurations 9 to 11, wherein
a position of the third resistance member in the second direction is between a position of the first resistance member in the second direction and a position of the second resistance member in the second direction.

Configuration 13

The sensor according to any one of Configurations 1 to 12, wherein
the absolute value of the third temperature coefficient is not more than ⅓ of the absolute value of the first temperature coefficient, and not more than ⅓ of the absolute value of the second temperature coefficient, Configuration 14

The sensor according to any one of Configurations 1 to 13, wherein
the absolute value of the first temperature coefficient is not less than 300 ppm/K,
the absolute value of the second temperature coefficient is not less than 300 ppm/K, and
the absolute value of the third temperature coefficient is not more than 100 ppm/K.

Configuration 15

The sensor according to Configuration 14, wherein
the absolute value of the third temperature coefficient is not more than 50 ppm/K.

Configuration 16

The sensor according to any one of Configurations 1 to 15, wherein
the third resistance member includes at least one selected from the group consisting of Ni and Cr.

Configuration 17

The sensor according to any one of Configurations 1 to 16, wherein
the third resistance member includes Ni and Cr, and a composition ratio of Cr in the third resistance member is not less than 30 wt % and not more than 80 wt %.

Configuration 18

The sensor according to Configuration 16 or 17, wherein
the first resistance member and the second resistance member include at least one selected from the group consisting of Ti, TiN, Al, W, Si, Cu, Au, Pd and Pt.

Configuration 19

The sensor according to Configuration 3 or 5, wherein
the wiring member includes at least one selected from the group consisting of aluminum, copper and gold.

Configuration 20

The sensor according to any one of Configurations 1 to 19, further comprising:
a circuit part,
the circuit part including a differential amplifier including a first input and a second input,
a signal corresponding to a potential of the first resistance member being input to the first input, and
a signal corresponding to a potential of the second resistance member being input to the second input.

According to one embodiment, a sensor can be provided, in which accuracy improvement is possible.

Hereinabove, exemplary embodiments of the invention are described with reference to specific examples. However, the embodiments of the invention are not limited to these specific examples. For example, one skilled in the art may similarly practice the invention by appropriately selecting specific configurations of components included in sensors such as base bodies, elements, processors, etc., from known art. Such practice is included in the scope of the invention to the extent that similar effects thereto are obtained.

Further, any two or more components of the specific examples may be combined within the extent of technical feasibility and are included in the scope of the invention to the extent that the purport of the invention is included.

Moreover, all sensors practicable by an appropriate design modification by one skilled in the art based on the sensors described above as embodiments of the invention also are within the scope of the invention to the extent that the spirit of the invention is included.

Various other variations and modifications can be conceived by those skilled in the art within the spirit of the invention, and it is understood that such variations and modifications are also encompassed within the scope of the invention.

While certain embodiments have been described, these embodiments have been presented by way of example only, and are not intended to limit the scope of the inventions, Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the invention.

What is claimed is:

1. A sensor, comprising:
   a first element including a first resistance member and a first conductive member;
   a second element including a second resistance member;
   a third resistance member connected in series with the second resistance member; and
   a base body including a first base body region and a second base body region,
   an absolute value of a third temperature coefficient of a third resistance of the third resistance member being smaller than an absolute value of a first temperature coefficient of a first resistance of the first resistance member,
   the absolute value of the third temperature coefficient being smaller than an absolute value of a second temperature coefficient of the second resistance member,
   the third resistance being lower than a second resistance of the second resistance member,
   the first element being provided in the first base body region,
   a first gap being provided between the first base body region and the first resistance member,
   the second element being provided in the second base body region, and
   a second direction from the first base body region to the second base body region crossing a first direction from the first base body region to the first resistance member.

2. The sensor according to claim 1, wherein
   the third resistance is lower than the first resistance.

3. The sensor according to claim 1, further comprising:
   a wiring member electrically connected with the second resistance member and the third resistance member,
   a wiring resistance of the wiring member being lower than the third resistance.

4. The sensor according to claim 3, wherein
   the wiring member includes at least one selected from the group consisting of aluminum, copper and gold.

5. The sensor according to claim 1, wherein
   a first resistance of the first resistance member changes due to temperature rise of the first resistance member due to a current flowing through the first conductive member.

6. The sensor according to claim 5, wherein
   the first resistance changed due to the temperature rise changes depending on a state of gas around the first element.

7. The sensor according to claim 1, wherein
   the second element further Includes a second conductive member.

8. The sensor according to claim 1, wherein
   a second gap is provided between the second base body region and the second resistance member.

9. The sensor according to claim 1, wherein
   a planar shape of the second element in a plane crossing the first direction is substantially same as a planar shape of the first element.

10. The sensor according to claim 1, wherein
    a position of the third resistance member in the second direction is between a position of the first resistance member in the second direction and a position of the second resistance member in the second direction.

11. The sensor according to claim 1, wherein
    the absolute value of the third temperature coefficient is not more than ⅓ of the absolute value of the first temperature coefficient, and not more than ⅓ of the absolute value of the second temperature coefficient.

12. The sensor according to claim 1, wherein
    the absolute value of the first temperature coefficient is not less than 300 ppm/K,
    the absolute value of the second temperature coefficient is not less than 300 ppm/K, and
    the absolute value of the third temperature coefficient is not more than 100 ppm/K.

13. The sensor according to claim 12, wherein
    the absolute value of the third temperature coefficient is not more than 50 ppm/K.

14. The sensor according to claim 1, wherein
    the third resistance member includes at least one selected from the group consisting of Ni and Cr.

15. The sensor according to claim 14, wherein
    the first resistance member and the second resistance member include at least one selected from the group consisting of TI, TiN, Al, W, Si, Cu, Au, Pd and Pt.

16. The sensor according to claim 1, wherein
    the third resistance member includes Ni and Cr, and a composition ratio of Cr in the third resistance member is not less than 30 wt % and not more than 80 wt %.

17. The sensor according to claim 1, further comprising:
    a circuit part,
    the circuit part including a differential amplifier including a first input and a second input,
    a signal corresponding to a potential of the first resistance member being input to the first input, and
    a signal corresponding to a potential of the second resistance member being input to the second input.

* * * * *